(12) United States Patent
Kambham

(10) Patent No.: US 10,561,317 B2
(45) Date of Patent: Feb. 18, 2020

(54) DEVICE FOR COMPREHENSIVE HEALTH MONITORING

(71) Applicant: Meghana Kambham, Hyderabad (IN)

(72) Inventor: Meghana Kambham, Hyderabad (IN)

( * ) Notice: Subject to any disclaimer, the term of this patent is extended or adjusted under 35 U.S.C. 154(b) by 62 days.

(21) Appl. No.: 15/330,993

(22) Filed: Dec. 9, 2016

(65) Prior Publication Data

US 2018/0271369 A1 Sep. 27, 2018
US 2019/0167104 A9 Jun. 6, 2019

(30) Foreign Application Priority Data

Sep. 16, 2016 (IN) .............................. 201641031607

(51) Int. Cl.
| | |
|---|---|
| *A61B 5/00* | (2006.01) |
| *A61B 5/0402* | (2006.01) |
| *A61B 5/021* | (2006.01) |
| *G16H 40/67* | (2018.01) |
| *G16H 10/60* | (2018.01) |
| *G16H 50/20* | (2018.01) |
| *A61B 1/05* | (2006.01) |
| *A61B 5/0205* | (2006.01) |
| *A61B 5/0428* | (2006.01) |
| *A61B 5/145* | (2006.01) |
| *A61B 5/1455* | (2006.01) |
| *A61B 7/04* | (2006.01) |
| *G06K 9/20* | (2006.01) |

(Continued)

(52) U.S. Cl.
CPC .............. *A61B 5/0022* (2013.01); *A61B 1/05* (2013.01); *A61B 5/0077* (2013.01); *A61B 5/021* (2013.01); *A61B 5/0205* (2013.01); *A61B 5/0402* (2013.01); *A61B 5/0428* (2013.01); *A61B 5/14535* (2013.01); *A61B 5/14551* (2013.01); *A61B 5/4833* (2013.01); *A61B 5/4848* (2013.01); *A61B 5/7282* (2013.01); *A61B 5/7445* (2013.01); *A61B 7/04* (2013.01); *G06K 9/209* (2013.01); *G06K 9/344* (2013.01); *G06K 9/36* (2013.01); *G06K 9/78* (2013.01); *G09B 21/003* (2013.01); *G16H 10/60* (2018.01); *G16H 40/67* (2018.01); *G16H 50/20* (2018.01); *A61B 2505/07* (2013.01); *A61B 2560/0462* (2013.01); *A61B 2562/22* (2013.01); *G06K 2209/01* (2013.01)

(58) Field of Classification Search
CPC ... A61B 5/0022; A61B 5/0205; A61B 5/0035; A61B 5/0402; A61B 5/0404
See application file for complete search history.

(56) References Cited

U.S. PATENT DOCUMENTS

2008/0255430 A1\* 10/2008 Alexandersson .. A61B 5/02055
600/300
2012/0130196 A1\* 5/2012 Jain .................... A61B 5/0022
600/300

(Continued)

*Primary Examiner* — Tammie K Marlen
(74) *Attorney, Agent, or Firm* — Cassandra T. Swain; Phong Dinh

(57) ABSTRACT

Implementations described herein disclose a method for direct screening and monitoring of health parameters of multiple individual subjects in a remote location with easy access and periodic visits by such multiple individual subjects, where such remote location is not a healthcare facility. Furthermore, an apparatus disclosed herein enables remote health monitoring of individual subjects including children outside the confines of a healthcare facility.

20 Claims, 10 Drawing Sheets

(51) Int. Cl.
*G06K 9/34* (2006.01)
*G06K 9/36* (2006.01)
*G06K 9/78* (2006.01)
*G09B 21/00* (2006.01)

(56) References Cited

U.S. PATENT DOCUMENTS

| | | | | |
|---|---|---|---|---|
| 2013/0281798 A1* | 10/2013 | Rau | .................. | A61B 5/4884 |
| | | | | 600/301 |
| 2014/0371544 A1* | 12/2014 | Wu | .................. | A61B 5/0077 |
| | | | | 600/301 |
| 2016/0278706 A1* | 9/2016 | Okamoto | ........... | G08B 21/0423 |

\* cited by examiner

DEVICE FOR COMPREHENSIVE HEALTH MONITORING

BACKGROUND

Healthcare technology and methods have advanced significantly over last century. Modern healthcare involves a variety of health monitoring devices for collecting an individual subject's health condition parameters. Such sensing devices, such as blood pressure monitoring devices, blood sugar monitoring devices, oxygen level monitoring devices, etc., allow a health care provider to collect, monitor, and record such data over long periods of time to generate more accurate individual subject profile and to assess the individual subject's health condition. Furthermore, advances in telecommunication technology allows for communicating information in real time over long distance and from remote locations.

However, in spite of the developments in health care and telecommunications technologies, a very large population of individual subjects, specifically poor children living remote areas, of a large number of developing countries do not have proper access to basic healthcare services in a timely manner.

SUMMARY

Implementations described herein disclose a method for direct monitoring of health parameters of multiple individual subjects in a remote location with easy access and periodic visits by such multiple individual subjects, where such remote location is not a healthcare facility.

Furthermore, an apparatus disclosed herein enables remote health monitoring of individual subjects including children outside the confines of a healthcare facility. Providing such remote health care monitoring apparatus eliminates the need of a healthcare provider and provides credible health related data, which enables a healthcare provider from anywhere to diagnose the individual subject and prescribe appropriate healthcare regimen.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

Example embodiments are illustrated in referenced figures of the drawings. It is intended that the embodiments and figures disclosed herein are to be considered illustrative rather than restrictive.

DETAILED DESCRIPTIONS

Figure 1:
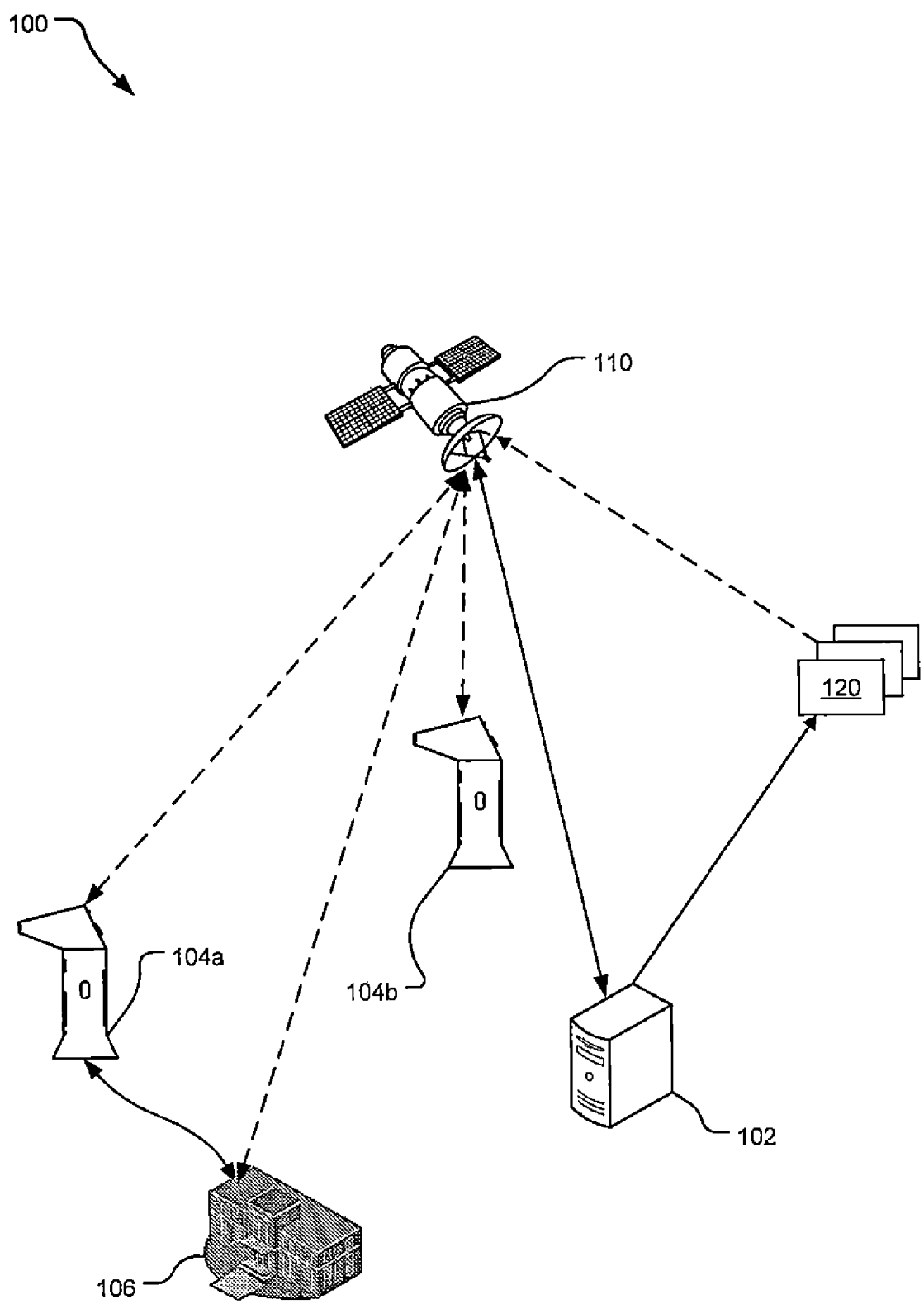
FIG. 1 illustrates an example implementation of a system for providing remote healthcare.

As utilized herein, terms "component," "system," "interface," and the like are intended to refer to a computer-related entity, either hardware, software (e.g., in execution), and/or firmware. For example, a component can be a process running on a processor, a processor, an object, an executable, a program, an app, and/or a computer (which may also be a mobile device). By way of illustration, both an application running on a server and the server can be a component. One or more components can reside within a process and a component can be localized on one computer and/or distributed between two or more computers.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

It is very important to monitor and track the health condition of children in their formative years. One of the best avenues for monitoring the health is at the schools. The health screening and monitoring of child at schools is currently completely ignored. A child is taken by parent to a physician when the health condition worsens. It might be more appropriate and efficient to monitor and track the vitals and health indicators of the child at school directly on a regular and periodic basis. The remote health monitoring system disclosed herein provides an integrated workflow for monitoring the vitals and health parameters of children on a regular and periodic basis directly in the school.

The remote monitoring method first determines the behavioral characteristics and health status of the child using a comprehensive extensive questionnaire. This helps first to set baseline of the current health status of the child. One of the embodiment provides for regular and periodic measurement and monitoring of the health status of the child. The health condition of the child is captured by the observations of any acute incidence or abnormal behavior. This is done on continuous basis by the teachers at a school and by the parents at the home of the child. Furthermore, the teachers and/or parents can also input data in the health report card of the child as and when necessary. This ensures continuous observation and monitoring.

The remote health monitoring system also utilizes a number of wireless, portable vital monitor devices to capture the vitals and health parameters of the child. This is done in regular intervals to get periodic readings of the vitals and health parameters. The regular recording of these parameters also provides for analyzing and predicting the trends for the various parameters. This then can be an early predictor or catching health anomalies early on even before their actual onset. Thus, the remote healthcare monitoring system disclosed herein provides ubiquitous, regular and periodic data capture using a variety of sensors and continuous feedbacks and capture of acute incidences by teachers, parents and caregivers.

In an implementation, the parameters are then passed through a clinical decision support system (CDSS) for determining if the parameters are in their normal or abnormal range. This helps to determine provisional health conditions, and also provisional diagnosis. If the health parameters are normal, then these data are then fed into the internal knowledge database portal. If the parameters could be improved, the CDSS suggests whether the parents have to go for confirmatory test for final diagnosis. After final diagnosis is confirmed, the CDSS searches appropriate 'good health-habit' nudges, to persuade for better health attainment.

One of the embodiment of the remote healthcare system also offers appropriate educated content and customized health home works when the health parameters are not within the normal range. These contents are provided to the child and the care providers, such as parents and teachers. The child is also followed up on the health activities related to the home works. The system also regularly and continuously monitors the readings through the health homework duration to ascertain and assure that the exercises are improving the child health parameters. The health parameters are then monitored over time to check for progress. Long sustained practices, exercises and behavior by the child are then checked to see if they have been inculcated into the child as habits. Specific feedback and closed loop mechanism (homework and its related follow up) are incorporated to help and guide the child to progress and improve their health parameters.

If the parameters are determined to be in the abnormal range, the internal knowledge database portal is analyzed to determine the first course of corrective actions. The parent and the family doctor are then intimated promptly. The follow up are then monitored in closed loop mechanism to help get the child quickly back to normal health. This workflow helps to determine the ill health conditions at its early stages so that they can be promptly attended to with the right medical attention.

These health parameters data are also captured and tracked on regular basis over long durations (several years). This voluminous data is analyzed using data analysis, machine learning approaches to get historical trends of the different vital parameters. The healthcare monitoring system also analyzes the parameters to determine regionalized and personalized (individual specific) health parameter ranges. Additionally, the system normalizes the parameters for each child against its historical reading to determine and monitor personalized health parameter trends. An implementation of the system also gives personalized suggestions to the child that best suit the child's current health parameter conditions.

The system also determines the personalized rate of improvement for each child based on the current personalized scenario and the improvements that the child makes using the health homework tasks and exercises provided to the child. When a child starts taking the health exercise, the child may go through the stages of trans-theoretical model (TTM)-denial, action till reversal. An implementation of the system disclosed herein identifies the TTM stage of the child and provides the parent or teacher the appropriate messaging to respond to the TTM stage as appropriate.

Different children could be in different phase pf the TTM. An implementation of the system disclosed herein forms virtual communities using a number of TTM profiles. Yet alternatively, the system generates group therapy using the different profiles, peer influence, peer pressure, and social contagion. For example, the system generates group of asthmatics, autistic, obese, type one diabetics, myopic, etc., and for each group generates one or more group therapies. Additionally, the system enrolls the kids into these groups, identifies group flag bearer and uses such group flag bearer to persuade good healthy habits among the member children in such groups.

For example, the system may also identify the top performers as those that are effectively able to follow the health suggestions effectively and then translate them into effective improvements in their health parameters. The system identifies these top performer children and rewards them as star performers. Subsequently the system showcases the top performers as role models for the rest of the children to emulate.

The integrated holistic workflow used by the remote healthcare monitoring and delivery system disclosed herein helps in maintaining and improving the health of children. The system also helps in early determination of any health related condition and in taking appropriate corrective measures to address the health condition of the children. The remote healthcare monitoring and delivery system also helps inculcating good health practices in children and allows children to learn the best methods to maintain and improve their health from other children.

FIG. 1 illustrates an example implementation of a system 100 for providing remote healthcare. Specifically, the system 100 includes a plurality of remote health monitoring modules 104a, 104b ("104") that may be used to provide health diagnosis and preventive services to individual subjects. For example, such individual subjects may be children that have little or no access to healthcare facility. The remote health monitoring modules 104 may be mobile devices, mobile kiosks, stationary kiosks, etc. In the illustrated implementation, such remote health monitoring modules 104 may be configured to collect a plurality of individual subject health parameters.

The remote health monitoring modules 104 may be used to collect such health parameters at a location other than a healthcare facility, such as for example, an educational facility 106. The healthcare parameters collected by the remote health monitoring modules 104 may be transmitted via a wireless manner, such as by satellite 110, or other wireless communication manner to a computing facility 102 that collects such health parameters over time and performs one or more data analytics to generate individuals' diagnosis reports 120 that may be transmitted back to them wirelessly.

In one example implementation, the remote health monitoring modules 104 may be configured to include a plurality of sensors, such as an image sensor to capture image of an individual subject, wherein the image sensor is configured on an elongated tip configured at the top of the remote health monitoring module, a sound recorder to capture sound input from an individual subject, wherein the sound recorder is configured on a base configured at the bottom of the remote health monitoring module, etc. The remote health monitoring modules 104 may also include a memory to store the health parameters collected by such sensors and a wireless transmitter to communicate one or more health parameters wirelessly. Alternative implementations of the remote health monitoring module includes one or more input nodes configured to connect to an electrocardiogram (ECG) lead and a bio-fluid detector device including a pulse oximetry sensor and a hemoglobin monitor. Example implementations of such remote health monitoring modules 104 are further disclosed in detail below in FIGS. 5-8.

The computing facility 102 may store computer programs with instructions to perform various data analytics and analysis. For example, such instructions may include instructions to determine behavioral characteristics of one or more individual subjects, instructions to diagnose one or more health condition of an individual subject based on analysis of the one or more health parameters, instructions to generate a diagnosis of the one or more determined health condition, and instructions to monitor improvement to the one or more health condition of the individual subject based on continued analysis of the one or more health parameters. In other implementations, the computing device 102 also stores instructions to generate individual subject profiles for a plurality of individual subjects, classify on or more of the plurality of individual subjects into one or more peer groups, and develop one or more exercises for the one or more peer groups. Furthermore, it may also store instructions to determine a leader for each of the one or more peer groups based on adherence of the peer group participants with the exercise and to showcase one or more rewards given to the peer group leader to the other members of the peer group.

Figure 2:
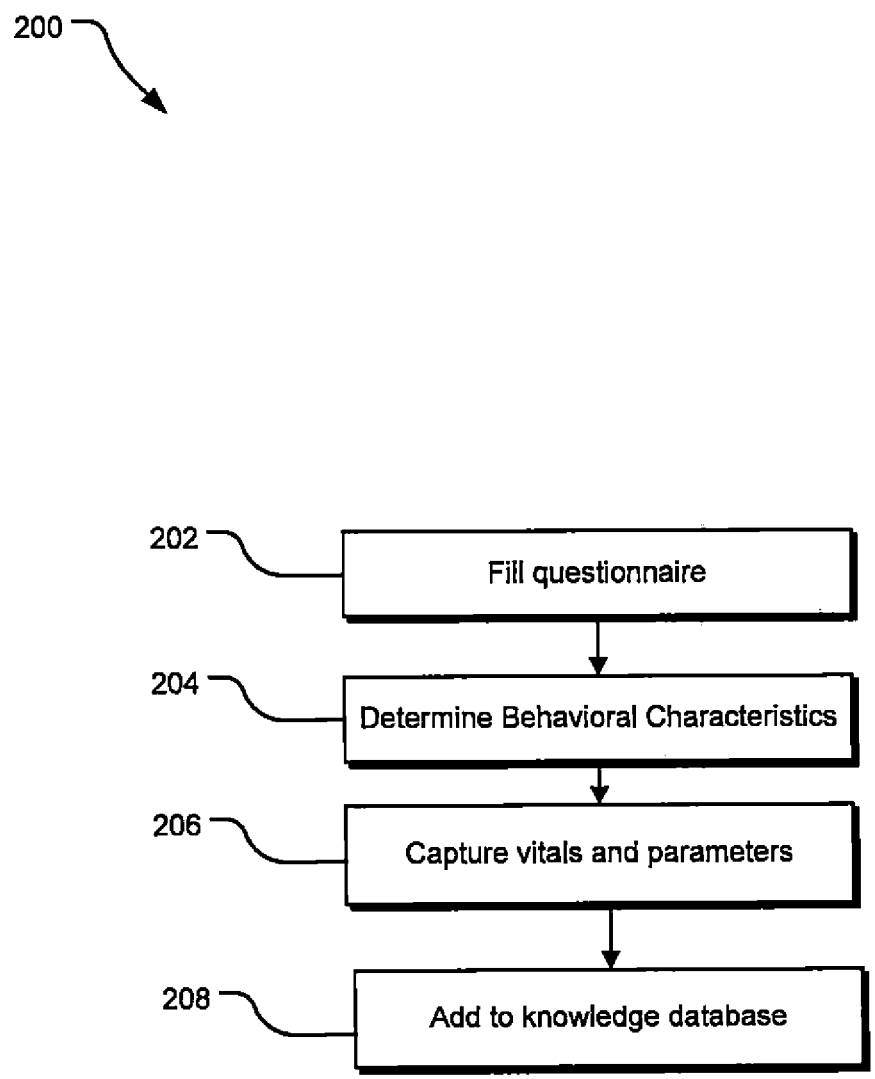
FIG. 2 illustrates an example routine operations of the remote healthcare delivery system disclosed herein.

FIG. 2 illustrates example routine operations 200 of the remote healthcare delivery system disclosed herein. Such operations 200 may be undertaken by a user, such as a teacher, a parent, a guardian, or other individual who is taking care of an individual, such as a child at a remote facility such as a school, a home of the child, etc. An operation 202 fills out a questionnaire with questions about the individual's health history as well as other health and lifestyle related data. An operation 204 determines the individual's behavioral characteristics, such as weather an individual child active, shy, athletic, leader, etc. An operation 206 captures vitals and other health parameters of the individual and the information collected at operations 202-206 are added to the knowledge database at an operation 208.

In one implementation, the operations 202-208 are performed at an educational facility using a remote health monitoring module, such as the one disclosed in further detail below in FIGS. 5-8. The information may be transmitted wirelessly to a remote computing device that stores the data and performs one or more data analytics using the data.

Figure 3:
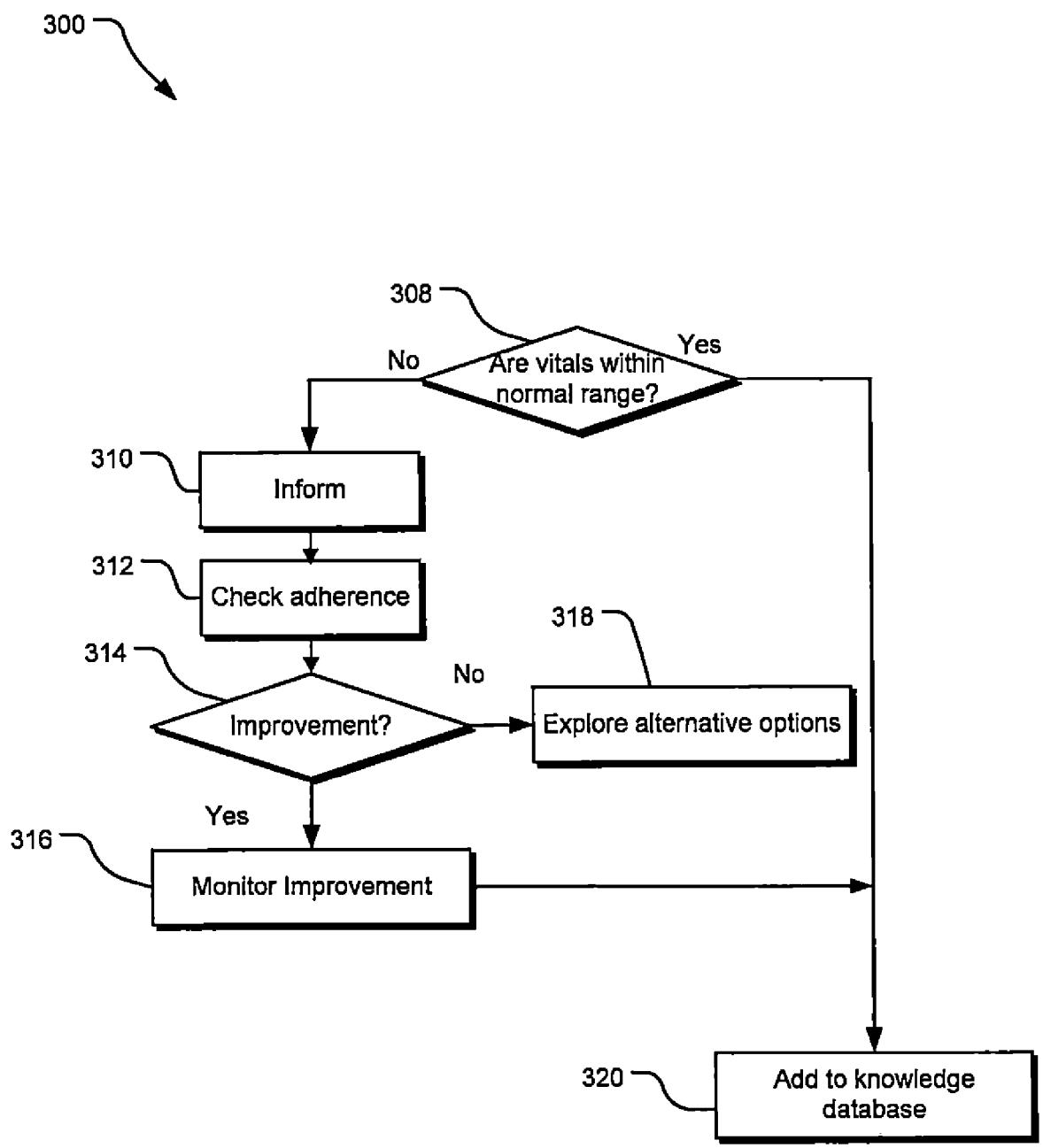
FIG. 3 illustrates example operations in response to abnormal observation for the remote healthcare delivery system disclosed herein.

FIG. 3 illustrates example operations 300 in response to abnormal observation for the remote healthcare delivery system disclosed herein. Specifically, a determining operation 308 may determine if the individual's vitals (such as blood pressure, oxygen level, etc.) are within a normal range. If the vitals are within a normal range, they are added to a knowledge database at an operation 320. If the vitals are not within a normal range, an operation 310 informs a healthcare provider, such as a nurse, a physician, etc. The healthcare provider may prescribe a healthcare regimen, treatment, etc. For example, such regimen may include specific diet, exercise, medicine, lifestyle, etc. An operation 312 checks the individual's adherence to such regimen.

An operation 314 periodically monitors the vitals to determine if there is any improvement in the individual's vitals. If there is any improvement, it is observed on a regular and periodic basis over time at operation 316 and the collected data is sent to the database. If there is no improvement, an operation 318 explores alternative options. An example of such alternative may be admittance of the individual to a healthcare facility, change in the regimen, etc.

Figure 4:
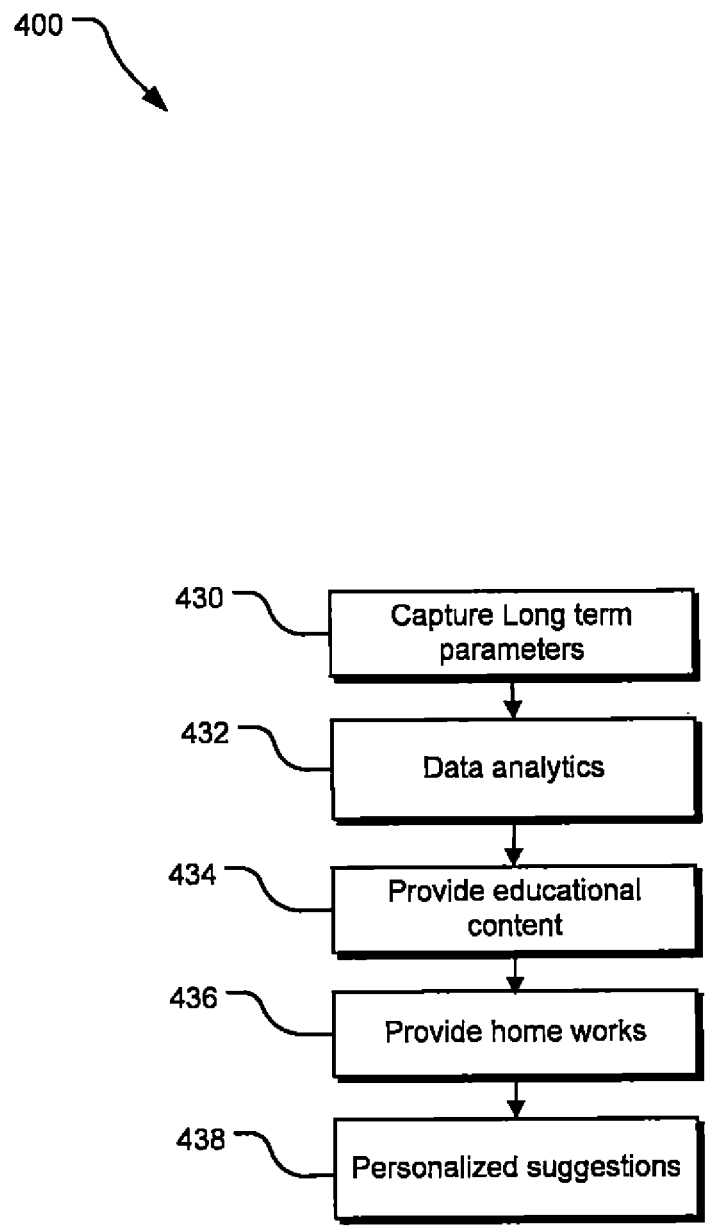
FIG. 4 illustrates example long-term operations of the remote healthcare delivery system disclosed herein.

FIG. 4 illustrates example long-term operations 400 of the remote healthcare delivery system disclosed herein. Specifically, an operation 430 captures long term health parameters of an individual and an operation 432 performs data analytics using the long term data. An operation 434 may provide educational content to the individual and an operation 436 may provide various home works to the individual. For example, the educational content may include guides on nutritional value of various food, benefits of various exercise, etc. The home works may include, for example, questions to determine if the individual understands the educational content. An operation 438 may provide personalized suggestions to the individual or to the individual's parent that may result in improvement in the health of the individual.

Figure 5:
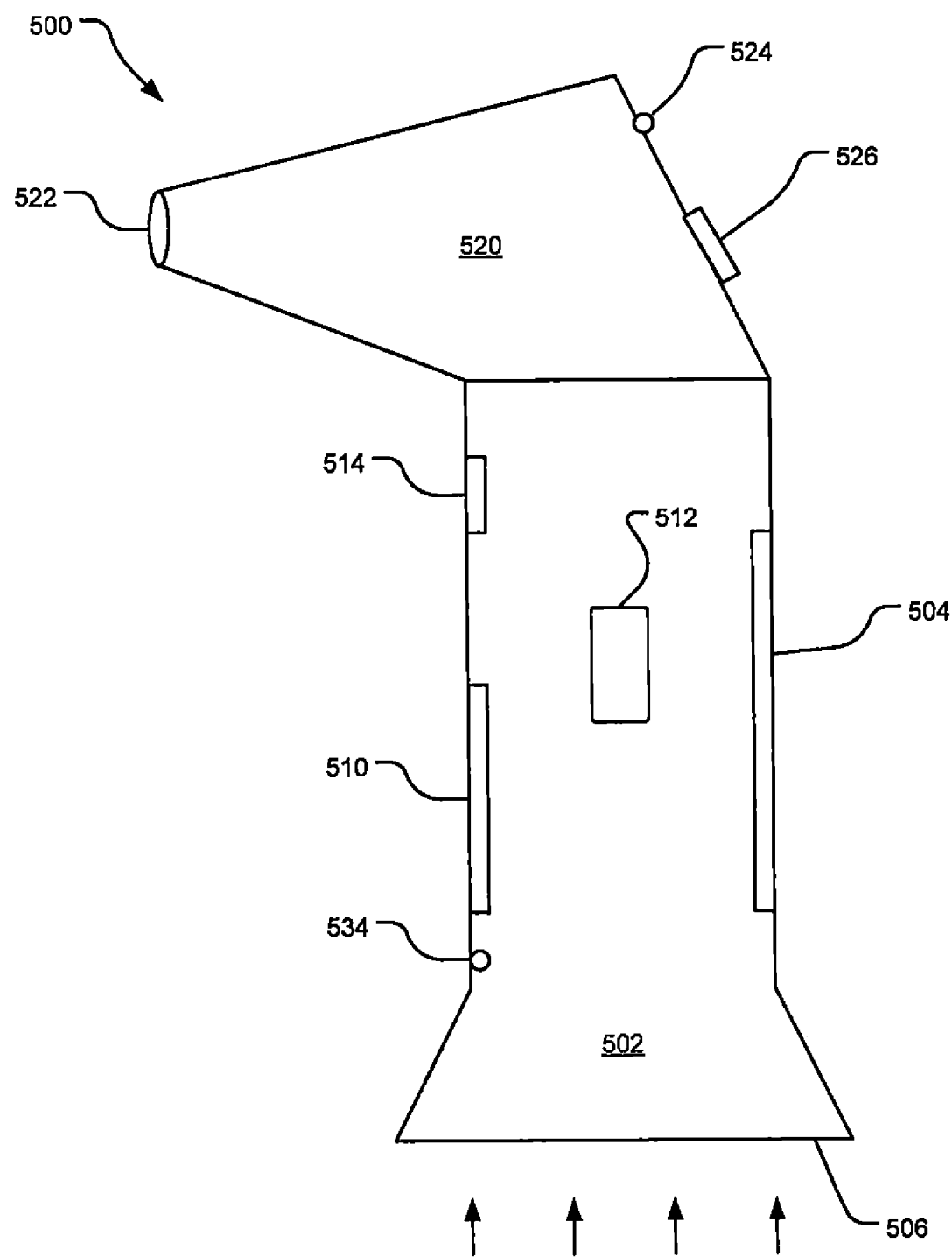
FIG. 5 illustrates a side view of an example kiosk apparatus for the remote healthcare delivery system disclosed herein.

FIG. 5 illustrates a side view of an example apparatus 500 for the remote healthcare delivery system disclosed herein. The apparatus 500 may be a mobile device, a kiosk, a stationary computing device, etc. Note that the components of the apparatus 500 as disclosed herein are for one example implementation. In an alternative implementation, more or less components may be provided. Yet alternatively, the location of the components may be different than as disclosed herein. Furthermore, the shape and the size of one of more components of the apparatus 500 may also be different compared to those disclosed in FIG. 5.

In one implementation, the apparatus 50 may be used at an educational facility to collect and monitor one or more health parameters of an individual, such as a child. In one example implementation, the apparatus 500 may be shaped to have a body 502 and a top 520. The body 502 may be of the shape and size that allows for mobility of the apparatus 500. For example, the body 502 may have a base 506 that is equipped with a sound detector that may be attached to a digital stethoscope. Thus, a user may attach the stethoscope to the base to detect and/or record sound of an individual's breathing, chest, etc.

The apparatus 500 may also include a lead or receptor 512 for an electrocardiogram (ECG) monitor that can be used to connect ECG sensors to the apparatus 500. In an example implementation, such receptor 512 is located on a side of the body 502. The apparatus 500 may also include a charger receptor 534 that allows the apparatus 500 to receive power from an outlet. In one implementation, the apparatus 500 uses rechargeable batteries 510 that may be used to provide power to various components and the rechargeable battery 510 may be charged using a charger though the charger receptor 534.

An implementation of the apparatus 500 also includes a pulse oximetry sensor 514 that may be used to measure pulse level. In an alternative implementation of the apparatus may 514 may be a bio-fluid detector device including a pulse oximetry sensor and a hemoglobin monitor. The apparatus 500 includes a display 504, such as a liquid crystal display (LCD) that shows various health parameters detected and/or collected by the various sensor components of the apparatus 500. The display 504 may also be used to show biographic, behavioral, or other parameters of the individual. In one implementation, the display 504 is located on a back surface of the apparatus 500.

The top section 520 of the apparatus 500 is configured to have conical shape with an elongated tip 522. The top section 520 may include a high quality image sensor that may be used to take images of an individual's inner throat, nose, ear, etc. Specifically, the elongated tip 522 allows inspection of such body parts. The top section 520 may also have a button 526 to operate the image sensor and an LED 524 to show an on/off status of the image sensor.

Figure 6:
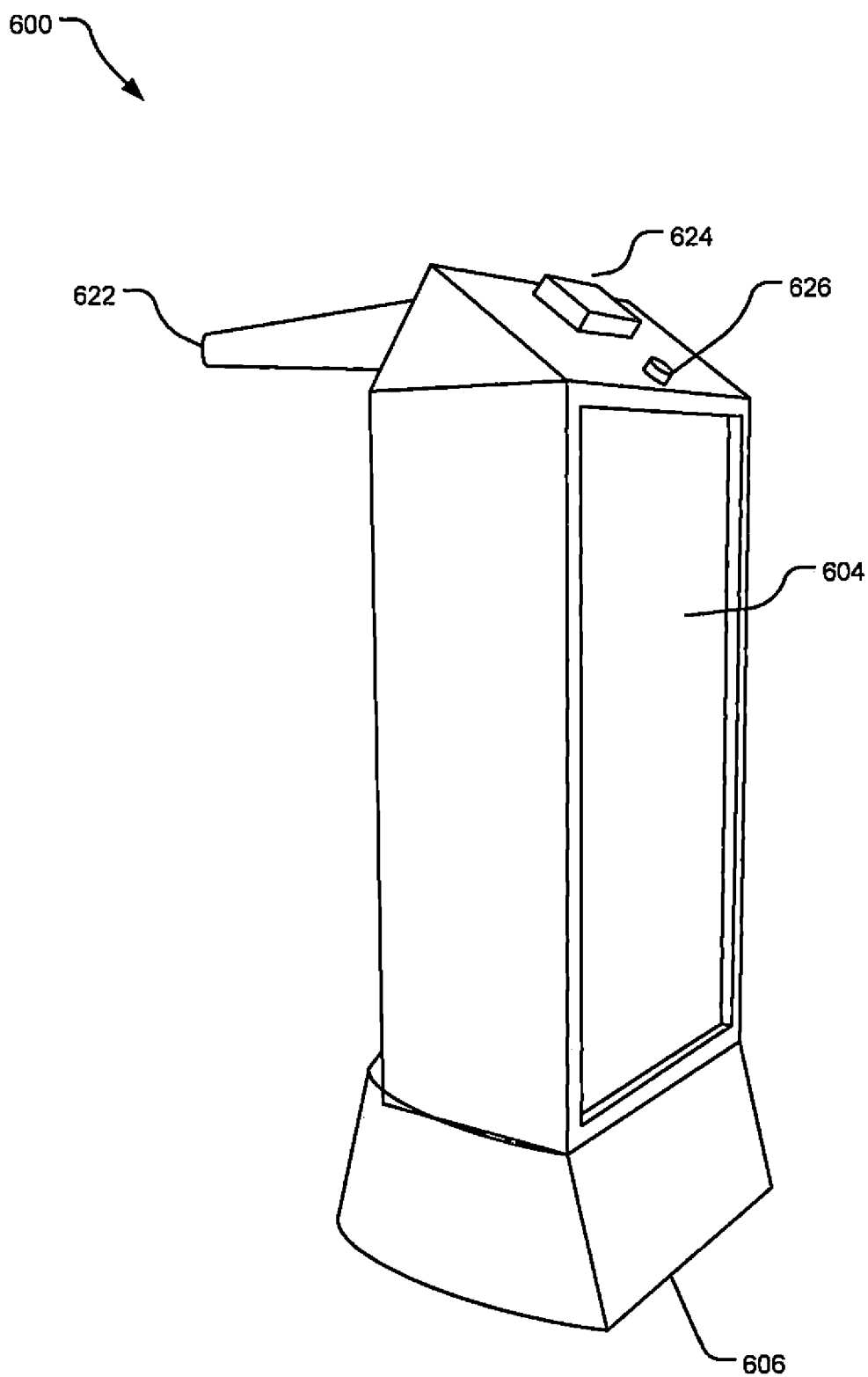
FIG. 6 illustrates a three-dimensional view of the example kiosk apparatus for the remote healthcare delivery system disclosed herein.

FIG. 6 illustrates a three-dimensional view of the example apparatus 600 for the remote healthcare delivery system disclosed herein. Specifically, FIG. 6 illustrates an LCD display 604 at the back of the apparatus, a base 606 that may be used to house a sound detector and to attach to a stethoscope, an elongated tip 622 housing a tiny high quality image sensor, a button 626 to operate such image sensor, and an LED light 624 to show the status of the image sensor. The image captured by the image sensor may be displayed on the LCD display 604.

Figure 7:
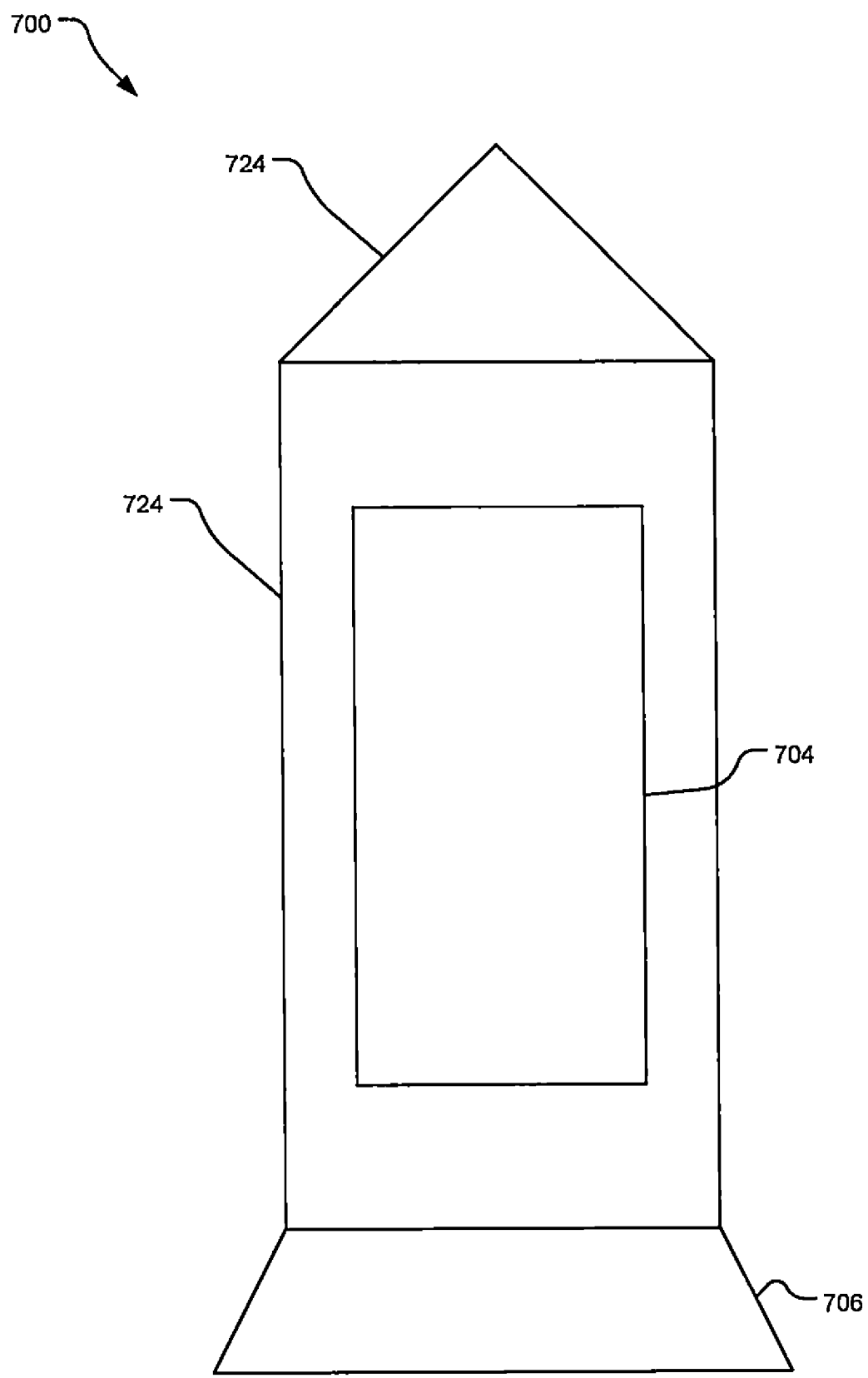
FIG. 7 illustrates a back view of the example kiosk apparatus for the remote healthcare delivery system disclosed herein.

FIG. 7 illustrates a back view of the example apparatus 700 for the remote healthcare delivery system disclosed herein. The apparatus 700 may have a top section 724 with a substantially triangular shape with a height of approximately 10 mm. The height of the body section 724 may be approximately 60 mm and the width of the body section 524 may be approximately 50 mm. The apparatus 700 may also include a base 706 to give stability to the apparatus 500 and to also collect sound signals from an individual, such as the individual's breathing, etc. The apparatus may have a housing 704 for a main CPU, sensors, wireless and other hardware peripherals. For example, such housing 704 may be 50 mm tall and 30 mm wide. Note that all of these measurements are only for one example implementation and they may vary in alternative implementations.

Figure 8:
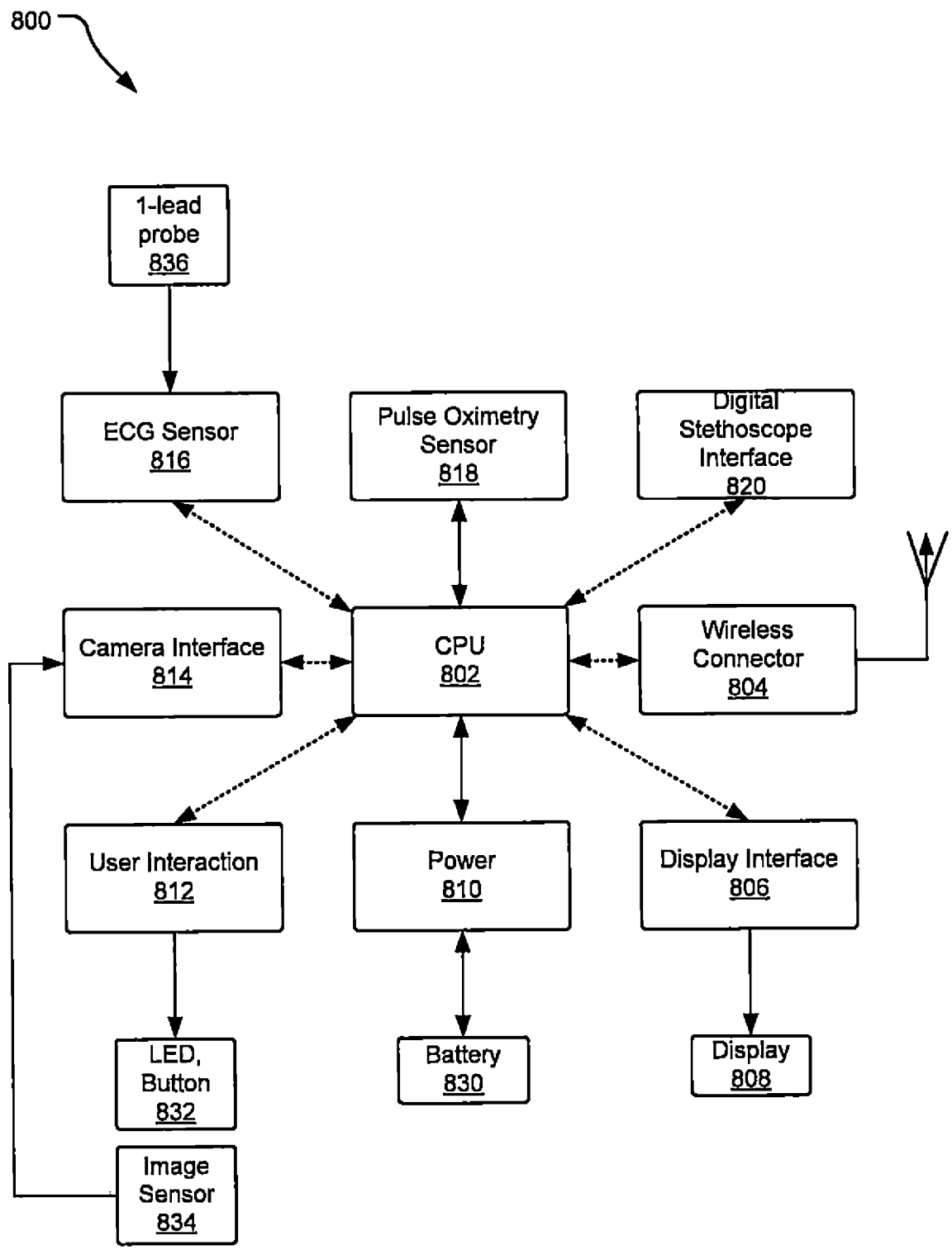
FIG. 8 illustrates an example block diagram of various components of the remote healthcare delivery system disclosed herein.

FIG. 8 illustrates an example block diagram of various components 800 of the remote healthcare delivery system disclosed herein. In one implementation, a CPU 802 may be connected to a wireless connector 804 that is connected to an antenna, a display interface 806 that is connected to a display, such as an LCD display 808, a power source 810 that is connected to battery 830 (which may be rechargeable battery). The CPU 802 may also be connected to a user interaction interface 812 that is connected to an LED button 832, a camera interface 814 that is connected to an image sensor 834, an ECG sensor 816 that may be connected to a probe 836 (such as a one-lead probe), a pulse oximetry sensor 818, and a digital stethoscope interface 820. Note that in alternative implementations, additional components may be connected to the CPU 802. In one implementation, all components disclosed in FIG. 8 are housed in a mobile health monitoring device, a kiosk for health monitoring, etc. The CPU 802 may also be connected to one or more storage components, such as RAM, ROM, other forms of memory, etc.

Figure 9:
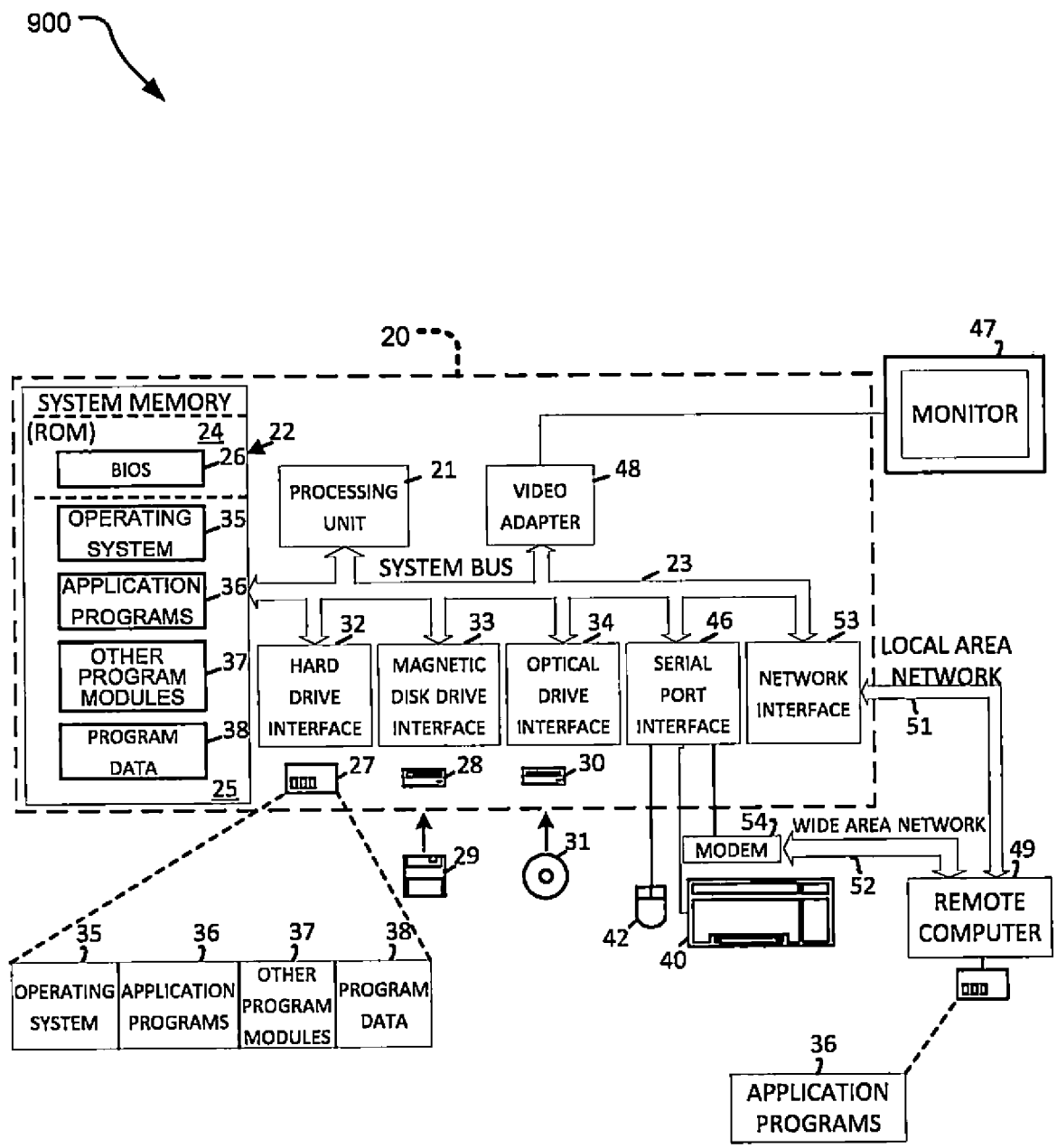
FIG. 9 illustrates an example system that may be useful in implementing the described technology.

FIG. 9 illustrates an example system 500 that may be useful in implementing the described technology for providing remote delivery of healthcare. The example hardware and operating environment of FIG. 9 for implementing the described technology includes a computing device, such as a general purpose computing device in the form of a computer 20, a mobile telephone, a personal data assistant (PDA), a tablet, smart watch, gaming remote, or other type of computing device. In the implementation of FIG. 5, for example, the computer 20 includes a processing unit 21, a system memory 22, and a system bus 23 that operatively couples various system components including the system memory to the processing unit 21. There may be only one or there may be more than one processing unit 21, such that the processor of computer 20 comprises a single central-processing unit (CPU), or a plurality of processing units, commonly referred to as a parallel processing environment. The computer 20 may be a conventional computer, a distributed computer, or any other type of computer; the implementations are not so limited.

The system bus 23 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 24 and random access memory (RAM) 25. A basic input/output system (BIOS) 26, containing the basic routines that help to transfer information between elements within the computer 20, such as during start-up, is stored in ROM 24. The computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated tangible computer-readable media provide non-volatile storage of computer-readable instructions, data structures, program modules and other data for the computer 20. It should be appreciated by those skilled in the art that any type of tangible computer-readable media may be used in the example operating environment.

A number of program modules may be stored on the hard disk drive 27, magnetic disk 29, optical disk 31, ROM 24, or RAM 25, including an operating system 35, one or more application programs 36, other program modules 37, and program data 38. A user may generate reminders on the personal computer 20 through input devices such as a keyboard 40 and pointing device 42. Other input devices (not shown) may include a microphone (e.g., for voice input), a camera (e.g., for a natural user interface (NUI)), a joystick, a game pad, a satellite dish, a scanner, or the like. These and other input devices are often connected to the processing unit 21 through a serial port interface 46 that is coupled to the system bus, but may be connected by other interfaces, such as a parallel port, game port, or a universal serial bus (USB). A monitor 47 or other type of display device is also connected to the system bus 23 via an interface, such as a video adapter 48. In addition to the monitor, computers typically include other peripheral output devices (not shown), such as speakers and printers.

The computer 20 may operate in a networked environment using logical connections to one or more remote computers, such as remote computer 49. These logical connections are achieved by a communication device coupled to or a part of the computer 20; the implementations are not limited to a particular type of communications device. The remote computer 49 may be another computer, a server, a router, a network PC, a client, a peer device or other common network node, and typically includes many or all of the elements described above relative to the computer 20. The logical connections depicted in FIG. 5 include a local-area network (LAN) 51 and a wide-area network (WAN) 52. Such networking environments are commonplace in office networks, enterprise-wide computer networks, intranets and the Internet, which are all types of networks.

When used in a LAN-networking environment, the computer 20 is connected to the local network 51 through a network interface or adapter 53, which is one type of communications device. When used in a WAN-networking environment, the computer 20 typically includes a modem 54, a network adapter, a type of communications device, or any other type of communications device for establishing communications over the wide area network 52. The modem 54, which may be internal or external, is connected to the system bus 23 via the serial port interface 46. In a networked environment, program engines depicted relative to the personal computer 20, or portions thereof, may be stored in the remote memory storage device. It is appreciated that the network connections shown are examples and other means of communications devices for establishing a communications link between the computers may be used.

In an example implementation, software or firmware instructions for providing remote healthcare delivery may be stored in memory 22 and/or storage devices 29 or 31 and processed by the processing unit 21. Rules for providing remote healthcare delivery may be stored in memory 22 and/or storage devices 29 or 31 as persistent datastores. For example, a remote healthcare delivery module may be implemented with instructions stored in the memory 22 and/or storage devices 29 or 31 and processed by the processing unit 21. Similarly, a GPS parameter processing module may also be implemented with instructions stored in the memory 22 and/or storage devices 29 or 31 and processed by the processing unit 21. The memory 22 may be used to store one or more remote healthcare delivery operations.

Figure 10:
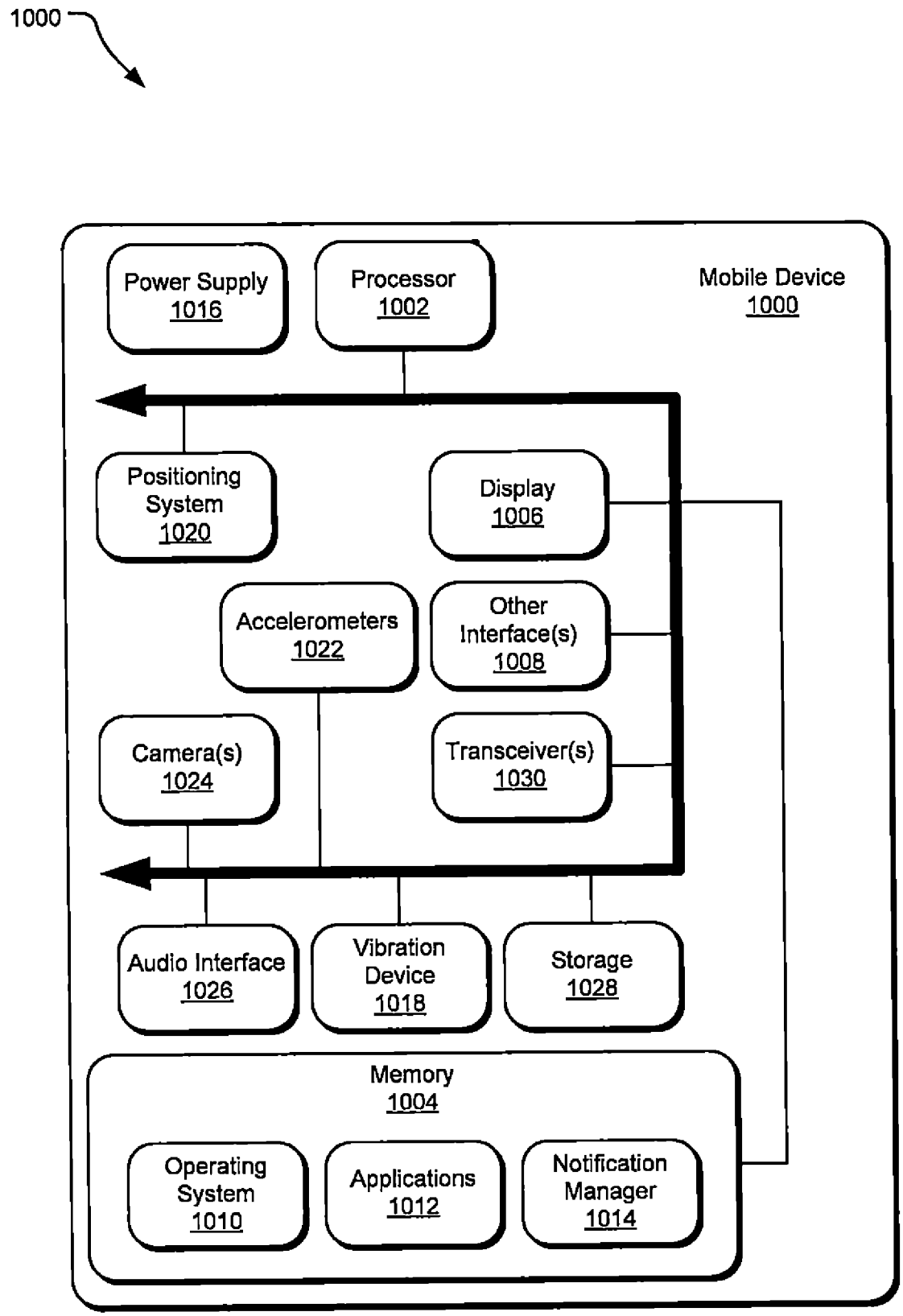
FIG. 10 illustrates an example mobile device that may be useful in implementing the described technology.

FIG. 10 illustrates another example system (labeled as a mobile device 1000) that may be useful in implementing the described technology. The mobile device 1000 includes a processor 1002, a memory 1004, a display 1006 (e.g., a touchscreen display), and other interfaces 1008 (e.g., a keyboard). The memory 1004 generally includes both volatile memory (e.g., RAM) and non-volatile memory (e.g., flash memory). An operating system 1010, such as the Microsoft Windows® Phone operating system, resides in the memory 1004 and is executed by the processor 1002, although it should be understood that other operating systems may be employed.

One or more application programs 1012 are loaded in the memory 1004 and executed on the operating system 1010 by the processor 1002. Examples of applications 1012 include without limitation email programs, scheduling programs, personal information managers, Internet browsing programs, multimedia player applications, etc. A notification manager 1014 is also loaded in the memory 1004 and is executed by the processor 1002 to present notifications to the user. For example, when a promotion is triggered and presented to the shopper, the notification manager 1014 can cause the mobile device 1000 to beep or vibrate (via the vibration device 1018) and display the promotion on the display 1006.

The mobile device 1000 includes a power supply 1016, which is powered by one or more batteries or other power sources and which provides power to other components of the mobile device 1000. The power supply 1016 may also be connected to an external power source that overrides or recharges the built-in batteries or other power sources.

The mobile device 1000 includes one or more communication transceivers 1030 to provide network connectivity (e.g., mobile phone network, Wi-Fi®, Bluetooth®, etc.). The mobile device 1000 also includes various other components, such as a positioning system 1020 (e.g., a global positioning satellite transceiver), one or more accelerometers 1022, one or more cameras 1024, an audio interface 1026 (e.g., a microphone, an audio amplifier and speaker and/or audio jack), and additional storage 1028. Other configurations may also be employed.

In an example implementation, a mobile operating system, various applications, and other modules and services may be embodied by instructions stored in memory 1004 and/or storage devices 1028 and processed by the processing unit 1002. User preferences, service options, and other data may be stored in memory 1004 and/or storage devices 1028 as persistent datastores.

In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

Some embodiments may comprise an article of manufacture. An article of manufacture may comprise a tangible storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of the logic may include various software elements, such as software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. In one embodiment, for example, an article of manufacture may store executable computer program instructions that, when executed by a computer, cause the computer to perform methods and/or operations in accordance with the described embodiments. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computer to perform a certain function. The instructions may be implemented using any suitable high-level, low-level, object-oriented, visual, compiled and/or interpreted programming language.

The system for remote healthcare delivery may include a variety of tangible computer-readable storage media and intangible computer-readable communication signals. Tangible computer-readable storage can be embodied by any available media that can be accessed by the remote desktop experience controller 115 and includes both volatile and nonvolatile storage media, removable and non-removable storage media. Tangible computer-readable storage media excludes intangible and transitory communications signals and includes volatile and nonvolatile, removable and non-removable storage media implemented in any method or technology for storage of information such as computer readable instructions, data structures, program modules or other data. Tangible computer-readable storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other tangible medium which can be used to store the desired information and which can be accessed by the remote desktop experience controller 115. In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A remote health monitoring and delivery system, comprising:
   a memory, the memory including a knowledge database;
   one or more processors configured to execute executable instructions to perform at least the following:
      receive a plurality of health parameters from one or more remote health monitoring devices, the one or more remote health monitoring devices including an image sensor to capture image of an individual subject, the image sensor configured on an elongated tip of the one or more remote health monitoring devices;
      store the plurality of health parameters in the knowledge database;
      determine behavioral characteristics of one or more individual subjects;
      diagnose one or more health conditions of an individual subject based on analysis of the plurality of health parameters;
      generate a diagnosis of one or more health conditions;
      monitor improvement to the one or more health conditions of the individual subject based on continued analysis of plurality of health parameters;
      generate individual subject profiles for a plurality of individual subjects;
      classify one or more of the plurality of individual subjects into one or more peer groups; and
      develop one or more exercises for the one or more peer groups.

2. The system of claim 1, wherein the one or more remote health monitoring devices are configured to collect the plurality of health parameters at an educational establishment.

3. The system of claim 1, wherein the one or more remote health monitoring devices include a sound detector to track and capture sound input from an individual subject, wherein the sound detector is configured on a base configured at the bottom of the one or more remote health monitoring devices.

4. The system of claim 1, wherein the one or more remote health monitoring devices include one or more input nodes configured to connect to an electrocardiogram (ECG) lead.

5. The system of claim 1, wherein the one or more remote health monitoring devices include a bio-fluid detector device including a pulse oximetry sensor and a hemoglobin monitor.

6. The system of claim 1, wherein the one or more remote health monitoring devices further comprising instructions to determine a leader for each of the one or more peer groups based on adherence of the peer group participants with exercise.

7. The system of claim 1, wherein the one or more remote health monitoring devices further comprising instructions to showcase one or more rewards given to a peer group leader to other members of the peer group.

8. A computer-implemented method for remote health monitoring and delivery, comprising:
   receiving a plurality of health parameters from one or more remote health monitoring devices, the one or more remote health monitoring devices including an image sensor to capture image of an individual subject, the image sensor configured on an elongated tip of the one or more remote health monitoring devices;
   storing the plurality of health parameters in a knowledge database;
   determining, using one or more processors, behavioral characteristics of one or more individual subjects;
   diagnosing, using the one or more processors, one or more health conditions of an individual subject based on analysis of the plurality of health parameters;
   generating, using the one or more processors, a diagnosis of one or more health conditions;
   monitoring, using the one or more processors, improvement to the one or more health conditions of the individual subject based on continued analysis of the plurality of health parameters;
   generating individual subject profiles for a plurality of individual subjects;
   classifying one or more of the plurality of individual subjects into one or more peer groups; and
   developing one or more exercises for the one or more peer groups.

9. The computer-implemented method of claim 8, wherein the one or more remote health monitoring devices are configured to collect the plurality of health parameters at an educational establishment.

10. The computer-implemented method of claim 8, wherein the one or more remote health monitoring devices include a sound detector to track and capture sound input from an individual subject, wherein the sound detector is configured on a base configured at the bottom of the one or more remote health monitoring devices.

11. The computer-implemented method of claim 8, wherein the one or more remote health monitoring devices include one or more input nodes configured to connect to an electrocardiogram (ECG) lead.

12. The computer-implemented method of claim 8, wherein the one or more remote health monitoring devices include a bio-fluid detector device including a pulse oximetry sensor and a hemoglobin monitor.

13. The computer-implemented method of claim 8, wherein the one or more remote health monitoring devices further comprising instructions to determine a leader for each of the one or more peer groups based on adherence of the peer group participants with exercise.

14. The computer-implemented method of claim 8, wherein the one or more remote health monitoring devices further comprising instructions to showcase one or more rewards given to a peer group leader to other members of the peer group.

15. One or more computer-readable media storing computer-executable instructions that upon execution cause one or more processors to perform acts comprising:
receiving a plurality of health parameters from one or more remote health monitoring devices, the one or more remote health monitoring devices including an image sensor to capture image of an individual subject, the image sensor configured on an elongated tip of the one or more remote health monitoring devices;
storing the plurality of health parameters in a knowledge database;
determining behavioral characteristics of one or more individual subjects;
diagnosing one or more health conditions of an individual subject based on analysis of the plurality of health parameters;
generating a diagnosis of one or more health conditions;
monitoring improvement to the one or more health conditions of the individual subject based on continued analysis of the plurality of health parameters;
generating individual subject profiles for a plurality of individual subjects;
classifying one or more of the plurality of individual subjects into one or more peer groups; and
developing one or more exercises for the one or more peer groups.

16. The one or more computer-readable media of claim 15, wherein the one or more remote health monitoring devices are configured to collect the plurality of health parameters at an educational establishment.

17. The one or more computer-readable media of claim 15, wherein the one or more remote health monitoring devices include a sound detector to track and capture sound input from an individual subject, wherein the sound detector is configured on a base configured at the bottom of the one or more remote health monitoring devices.

18. The one or more computer-readable media of claim 15, wherein the one or more remote health monitoring devices include one or more input nodes configured to connect to an electrocardiogram (ECG) lead.

19. The one or more computer-readable media of claim 15, wherein the one or more remote health monitoring devices include a bio-fluid detector device including a pulse oximetry sensor and a hemoglobin monitor.

20. The one or more computer-readable media of claim 15, wherein the one or more remote health monitoring devices further comprising instructions to determine a leader for each of the one or more peer groups based on adherence of the peer group participants with exercise.

* * * * *